United States Patent [19]

Felix et al.

[11] Patent Number: 5,254,309
[45] Date of Patent: Oct. 19, 1993

[54] STERILANT MIXTURE AND STERILIZATION METHOD

[75] Inventors: Vinci M. Felix, Kennett Square, Pa.; Tuneen Chisolm-Carter, New Castle, Del.

[73] Assignee: E. I. Du Pont de Nemours and Company, Wilmington, Del.; Praxair Tech., Inc., Danbury, Conn.

[21] Appl. No.: 12,790

[22] Filed: Feb. 2, 1993

Related U.S. Application Data

[63] Continuation of Ser. No. 920,034, Jul. 21, 1992, abandoned.

[51] Int. Cl.⁵ .................................. A61L 2/16
[52] U.S. Cl. ........................ 422/34; 422/37; 422/28; 252/DIG. 9
[58] Field of Search ............... 422/28, 34, 37; 252/372, DIG. 9

[56] References Cited

U.S. PATENT DOCUMENTS

| | | | |
|---|---|---|---|
| 2,891,838 | 6/1959 | Kaye | 422/34 |
| 3,359,159 | 12/1967 | Fulton et al. | 514/475 |
| 3,372,980 | 3/1968 | Satas | 422/2 |
| 3,989,461 | 11/1976 | Skocypec et al. | 422/34 X |
| 4,312,188 | 1/1982 | Swenson et al. | 62/160 |
| 4,541,943 | 9/1985 | Powell | 252/67 |
| 4,668,830 | 5/1987 | Desbois | 568/655 |
| 4,954,284 | 9/1990 | Batt et al. | 422/34 X |
| 4,971,716 | 11/1990 | Batt et al. | 422/37 X |
| 4,976,922 | 12/1990 | Chippett et al. | 422/34 |
| 5,039,485 | 8/1991 | Conviser et al. | 422/34 |

FOREIGN PATENT DOCUMENTS

| | | |
|---|---|---|
| 2009169 | 8/1990 | Canada . |
| 385798 | 9/1990 | European Pat. Off. . |
| 2-272086 | 11/1990 | Japan . |
| WO90-03807 | 4/1990 | PCT Int'l Appl. . |
| WO91-01764 | 6/1990 | PCT Int'l Appl. . |

*Primary Examiner*—Robert J. Warden
*Assistant Examiner*—E. Leigh Dawson
*Attorney, Agent, or Firm*—P. Michael Walker

[57] ABSTRACT

A sterilant mixture comprising 15 to 30 mole percent ethylene oxide and 70 to 85 mole percent 1,1,1,3,3,3-hexafluoropropane (HFC-236fa) and a sterilization method using same.

9 Claims, 2 Drawing Sheets

STERILANT MIXTURE AND STERILIZATION METHOD

This is a continuation, of application Ser. No. 07/920,034 filed Jul. 21, 1992, now abandoned.

BACKGROUND OF THE INVENTION

This invention relates generally to the field of sterilization and more particularly to sterilization based on the use of ethylene oxide.

Sterilization by the application of boiling water or steam to the article to be sterilized has been carried out for many years. More recently there has arisen in certain fields, such as in medicine and in space exploration, the need to employ a different sterilant because certain articles used in these fields cannot withstand the temperatures or the moisture associated with steam sterilization.

One sterilant that has become widely used is ethylene oxide because not only is it an effective sterilant but also its residues volatize relatively quickly from the article sterilized. Although ethylene oxide may be used by itself to carry out the sterilization, this is generally not done because ethylene oxide is highly flammable. Instead, ethylene oxide sterilant is generally used in a mixture with a flame retardant. The flame retardant, however, must complement the properties of the ethylene oxide or the beneficial effects of the ethylene oxide will be lost. Over the last two decades the flame retardant of choice for use with ethylene oxide in a sterilant mixture has been dichlorodifluoromethane, known in the industry as CFC-12. The most commonly used sterilant mixture comprises 27.3 mole percent (12 weight percent) ethylene oxide and 72.7 mole percent (88 weight percent) CFC-12. This mixture is commonly referred to in the industry as 12-88.

Recently a problem has arisen in the use of CFC-12 because it is one of the chlorofluorocarbons believed to cause significant damage to the ozone layer in the upper atmosphere. Accordingly, worldwide reduction and elimination of the use of CFC-12 is now underway. This has created a problem for the use of ethylene oxide as a sterilant.

Alternative flame retardants have been proposed, but they are not as effective as CFC-12 in that less ethylene oxide can be mixed with these alternatives before the mixture becomes flammable. For example, the maximum amount of ethylene oxide that may be mixed with either 1,1-dichloro-2,2,2-trifluoroethane (HCFC-123) or 1-chloro-1,2,2,2-tetrafluoroethane (HCFC-124) before the mixture becomes flammable is 23 mole percent. For pentafluoroethane (HFC-125), the maximum amount of ethylene oxide that can be added to HFC-125 before the mixture becomes flammable is 19 mole percent, and for 1,2,2,2-tetrafluoroethane (HFC-134a), the maximum amount of ethylene oxide is 12 mole percent.

Further, HCFC-123 and HCFC-124 both contain chlorine and therefore may adversely affect the Earth's atmosphere.

As mentioned above, ethylene oxide may be used by itself as a sterilant. However the explosion danger of such use makes it acceptable for only a relatively few applications at locations which have experienced and sophisticated handlers available at all times.

One flame retardant which is known for use with ethylene oxide is carbon dioxide. However, because of the characteristics of carbon dioxide, a non-flammable ethylene oxide-carbon dioxide mixture contains less than 40 percent of the ethylene oxide per unit volume as does 12-88. Thus, sterilization must be carried out either at higher pressures or for longer contact times. Furthermore, the large difference in the vapor pressures of ethylene oxide and carbon dioxide causes the mixture to separate upon withdrawal from the storage tank or cylinder, raising the danger of delivering a sterilant mixture rich in carbon dioxide, which will not sterilize, or rich in ethylene oxide, which is explosive.

It has now been found possible to provide an improved sterilant mixture employing ethylene oxide which overcomes the deficiencies of the known sterilants and to provide an improved sterilization method using a sterilant mixture employing ethylene oxide which overcomes the deficiencies of the known sterilization methods.

SUMMARY OF THE INVENTION

According to the present invention, there is provided a sterilant mixture which comprises from 15 to 30 mole percent ethylene oxide and from 70 to 85 mole percent 1,1,1,3,3,3-hexafluoropropane (HFC-236fa).

The present invention also provides a method for sterilizing an article which comprises contacting the article with an effective amount of a sterilant mixture comprising from 15 to 30 mole percent ethylene oxide and from 70 to 85 mole percent 1,1,1,3,3,3-hexafluoropropane.

The present invention is also directed to azeotropic or azeotrope-like compositions of ethylene oxide and HFC-236fa that may be used, for example, as a sterilant mixture.

The gas mixture of this invention may be used with any commonly employed sterilizer known to the art.

DETAILED DESCRIPTION

Figure 1:
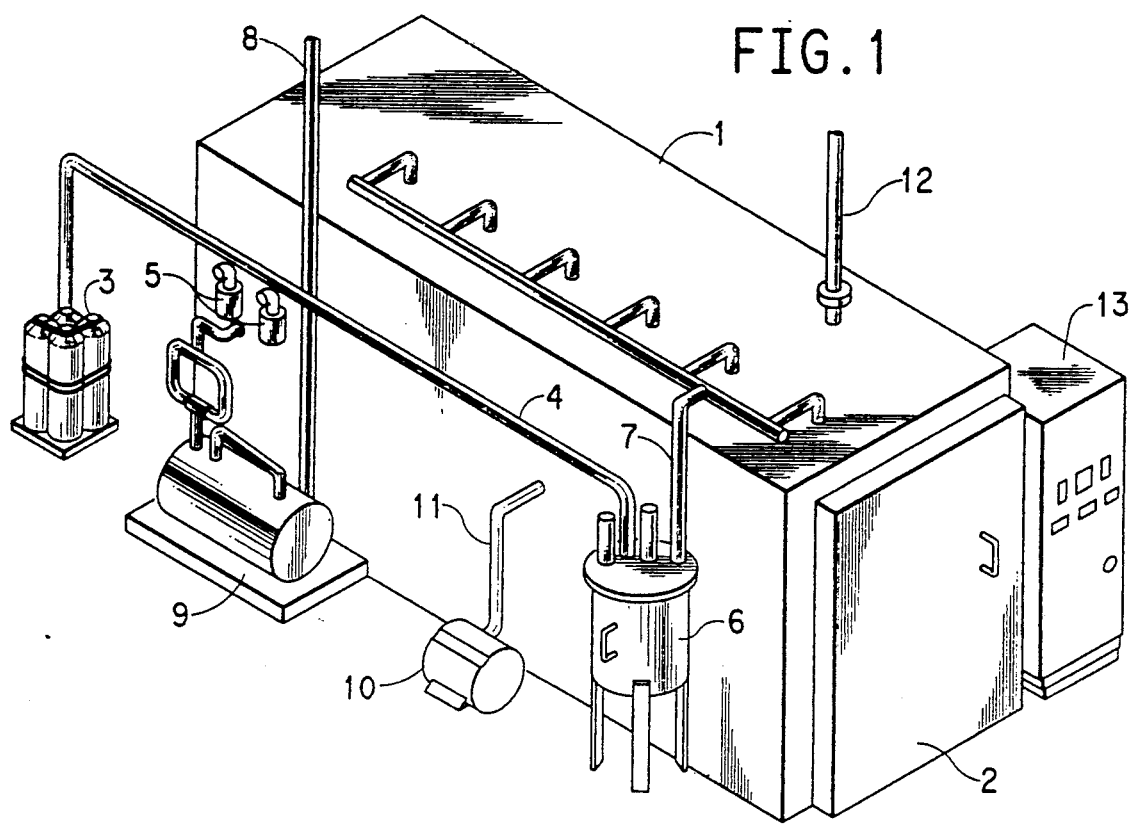
FIG. 1 is a schematic representation of one sterilizer apparatus with which the method of the present invention may be employed.

The present invention is a sterilant mixture and a method of sterilizing articles using the sterilant mixture. The sterilant mixture is generally used as a gas or vapor.

The sterilant mixture of this invention comprises from 15 to 30 mole percent, preferably from 20 to 26 mole percent, ethylene oxide and from 70 to 85 mole percent, preferably from 74 to 80 mole percent, 1,1,1,3,3,3-hexafluoropropane. The ethylene oxide acts as the active sterilizer while the halogenated compound, or compounds if a mixture is employed, acts as a flame retardant. At flame retardant concentrations less than the specified minimum, sufficient flame retardancy may not be present in the mixture to avoid a potentially dangerous situation, and at flame retardant concentrations greater than the specified maximum, effective sterilization may not be possible without the use of undesirably high temperatures, pressures and/or contact times.

Preferably the sterilant mixture of this invention comprises only ethylene oxide and HFC-236fa. However, the sterilant mixture may in addition contain chlorodifluoromethane to increase the vapor pressure or reduce the cost of the sterilant mixture. An increased vapor pressure may be desirable in some sterilization systems to propel the sterilant mixture into a sterilization chamber in a timely manner, particularly in a situation where the sterilant container temperature cannot be maintained at or about 21° C. (70° F.).

Other components which may be present in the sterilant mixture of the invention include inert nitrogen gas which may also be used to increase the pressure in the sterilant container in order to propel the sterilant mixture into the sterilization chamber.

The sterilant mixture of this invention may be used to sterilize a great many articles. Examples of medical equipment and materials which may be sterilized include diagnostic endoscopes; plastic goods such as syringes, gloves, test tubes, incubators and pacemakers; rubber goods such as tubing, catheters and sheeting; instruments such as needles, scalpels and oxygen tests; and other items such as dilators, pumps, motors and intraocular lenses. In addition, the sterilant mixture of this invention may be used as a fumigant for items outside the medical field. These items include certain foodstuffs, such as spices, and other items such as furs, bedding, paper goods, and transportation equipment such as the cargo area of airplanes, trains and ships.

The sterilant mixture of this invention is effective against all forms of life, particularly unwanted insects, bacteria, virus, molds, fungi, and other microorganisms. Among the most difficult organisms to kill is B. Subtilus sbs. niger spores; however, even these organisms are effectively destroyed by the sterilant mixture of the invention.

The sterilant mixture of this invention may be made using any effective mixing technique well known to those skilled in the art. For example, each compound of the mixture may be pumped gravimetrically through a manifold into a sterilant container, and the container rolled to intermix the compounds into a homogeneous mixture. Alternatively, the compounds may be pumped into a mixing tank, recirculated in the tank until a fully homogeneous mixture is formed, and then pumped from the mixing tank into a sterilant container.

The sterilant mixture of this invention may be packaged in any gas storage containers of suitable design such as U.S. Department of Transportation (DOT) Specification 4BA 240, 4BA 300, 4BW 240 or other DOT specification cylinders or trailers of suitable working pressure. The sterilant mixture may also be packaged in American Society of Mechanical Engineers (ASME) storage vessels.

The gas storage cylinder may be delivered to the use site holding the sterilant mixture at a pressure generally within the range of from about 207 to 345 kPa at 21° C. (30 to 50 pounds per square inch absolute (psia) at 70° F.), and connected through a series of valves, control valves, vaporizer and appropriate conduit to a sterilizer to carry out the sterilization.

The present invention will now be further described with reference to the accompanying drawings, but in no manner limited thereto.

Referring now to FIG. 1, the item or items to be sterilized are placed within sterilization chamber 1 through door 2. Sterilizers such as illustrated in FIG. 1 may range in size from desk-top models to room-size models and even larger. After the items are placed within sterilization chamber 1 and door 2 is shut, the chamber is heated generally to a temperature within the range of from 54° C. to 60° C. (130° F. to 140° F.). Generally, the higher the temperature the shorter is the required exposure time. After the chamber is brought up to temperature, a partial vacuum is drawn inside the chamber by pumping out air through vent 8 by vacuum pump 9. The air removal serves both to prevent dilution of the sterilant mixture and to reduce the exposure pressure. Creating the appropriate vacuum generally takes from about 5 to 45 minutes depending on the item to be sterilized since some items can be damaged by sudden pressure changes. Since a moist microorganism is more susceptible to the reaction of the sterilant, water vapor is employed. In FIG. 1, water vapor from steam source 10 may be injected into chamber 1 through conduit 11. The water vapor is used to create a relative humidity within the chamber within the range of from 30 to 80 percent.

Sterilant mixture is passed from a source such as cylinder 3 through conduit 4 and filters 5 to vaporizer 6 wherein it is converted to a vapor. From vaporizer 6, the sterilant mixture is passed through conduit 7 into sterilization chamber 1 for the sterilization. The pressure at which the sterilization takes place within chamber 1 may be from about 48 to 228 kPa (7 to 33 psia). The sterilization time will vary and is dependent upon a number of factors including temperature, pressure, humidity level, the specific sterilant mixture employed, and the material being sterilized. For example, some porous articles require shorter exposure time than do articles sealed in polyethylene bags. Moreover, some bacteria are especially resistant and thus take longer to destroy.

Following the required exposure time, the sterilant mixture is evacuated from the chamber by flushing with air, nitrogen, steam or carbon dioxide through inlet 12 and successive evacuation through conduit 8 by pump 9. The sterilized material is then removed from chamber 1 through door 2 and, if necessary, aerated for the removal of residual sterilant, before being used. The entire sterilization procedure may be monitored and controlled through control panel 13.

The present invention also relates to the discovery of azeotropic or azeotrope-like compositions of effective amounts of ethylene oxide and HFC-236fa to form an azeotropic or azeotrope-like composition at a specified temperature or pressure. These compositions may be used as sterilants.

It is recognized in the art that a composition is azeotropic or azeotrope-like if, after 50 weight percent of the composition is removed such as by evaporation or boiling off, the difference in vapor pressure between the original composition and the composition remaining after 50 weight percent of the original composition has been removed is less than 10 percent, when measured in absolute units. By absolute units, it is meant measurements of pressure and, for example, psia, atmospheres, bars, torr, dynes per square centimeter, millimeters of mercury, inches of water and other equivalent terms well known in the art.

Therefore, included in this invention are compositions of effective amounts of ethylene oxide and HFC-236fa such that after 50 weight percent of an original composition is evaporated or boiled off to produce a remaining composition, the difference in the vapor pressure between the original composition and the remaining composition is 10 percent or less.

Substantially constant boiling, azeotropic or azeotrope-like compositions of this invention comprise the following (at 25° C.): from 6 to 65, and preferably from 22 to 46 mole percent ethylene oxide and from 35 to 94, and preferably 54 to 78 mole percent HFC-236fa.

For purposes of this invention, "effective amount" is defined as the amount of each component of the inventive compositions which, when combined, results in the formation of an azeotropic or azeotrope-like composition. This definition includes the amounts of each component, which amounts may vary depending on the pressure applied to the composition so long as the azeotropic or azeotrope-like compositions continue to exist at the different pressures, but with possible different boiling points.

Therefore, effective amount includes the amounts, such as may be expressed in mole percentages, of each component of the compositions of the instant invention which form azeotropic or azeotrope-like compositions at temperatures or pressures other than as described herein.

By "azeotropic or azeotrope-like" composition is meant a constant boiling, or substantially constant boiling, liquid admixture of two or more substances that behaves as a single substance. One way to characterize an azeotropic or azeotrope-like composition is that the vapor produced by partial evaporation or distillation of the liquid has substantially the same composition as the liquid from which it was evaporated or distilled, that is, the admixture distills/refluxes without substantial composition change. Constant boiling or substantially constant boiling compositions, which are characterized as azeotropic or azeotrope-like, exhibit either a maximum or minimum boiling point, as compared with that of the non-azeotropic mixtures of the same components.

For the purposes of this discussion, azeotropic or constant-boiling is intended to mean also essentially azeotropic or essentially-constant boiling. In other words, included within the meaning of these terms is not only the true azeotrope, but also other compositions containing the same components in different proportions, which are azeotropic at other temperatures and pressures, as well as those equivalent compositions which are part of the same azeotropic system and are azeotrope-like in their properties. As is well recognized in this art, there is a range of compositions which contain the same components as the azeotrope, which will not only exhibit essentially equivalent properties for refrigeration and other applications, but which will also exhibit essentially equivalent properties to the true azeotropic composition in terms of constant boiling characteristics or tendency not to segregate or fractionate on boiling.

It is possible to characterize, in effect, a constant boiling admixture which may appear under many guises, depending upon the conditions chosen, by any of several criteria:

The composition can be defined as an azeotrope of A, B, C (and D . . . ) since the very term "azeotrope" is at once both definitive and limitative, and requires that effective amounts of A, B, C (and D . . . ) for this unique composition of matter which is a constant boiling composition.

It is well known by those skilled in the art, that, at different pressures, the composition of a given azeotrope will vary at least to some degree, and changes in pressure will also change, at least to some degree, the boiling point temperature. Thus, an azeotrope of A, B, C (and D . . . ) represents a unique type of relationship but with a variable composition which depends on temperature and/or pressure.

Therefore, compositional ranges, rather than fixed compositions, are often used to define azeotropes.

The composition can be defined as a particular weight percent relationship or mole percent relationship of A, B, C (and D . . . ), while recognizing that such specific values point out only one particular relationship and that in actuality, a series of such relationships, represented by A, B, C (and D . . . ) actually exist for a given azeotrope, varied by the influence of pressure.

An azeotrope of A, B, C (and D . . . ) can be characterized by defining the compositions as an azeotrope characterized by a boiling point at a given pressure, thus giving identifying characteristics without unduly limiting the scope of the invention by a specific numerical composition, which is limited by and is only as accurate as the analytical equipment available.

The azeotrope or azeotrope-like compositions of the present invention can be prepared by any convenient method including mixing or combining the desired amounts. A preferred method is to weigh the desired component amounts and thereafter combine them in an appropriate container.

The following Examples and comparative Examples serve to further illustrate or distinguish the invention. They are not intended to be limiting.

EXAMPLE 1

Figure 2:
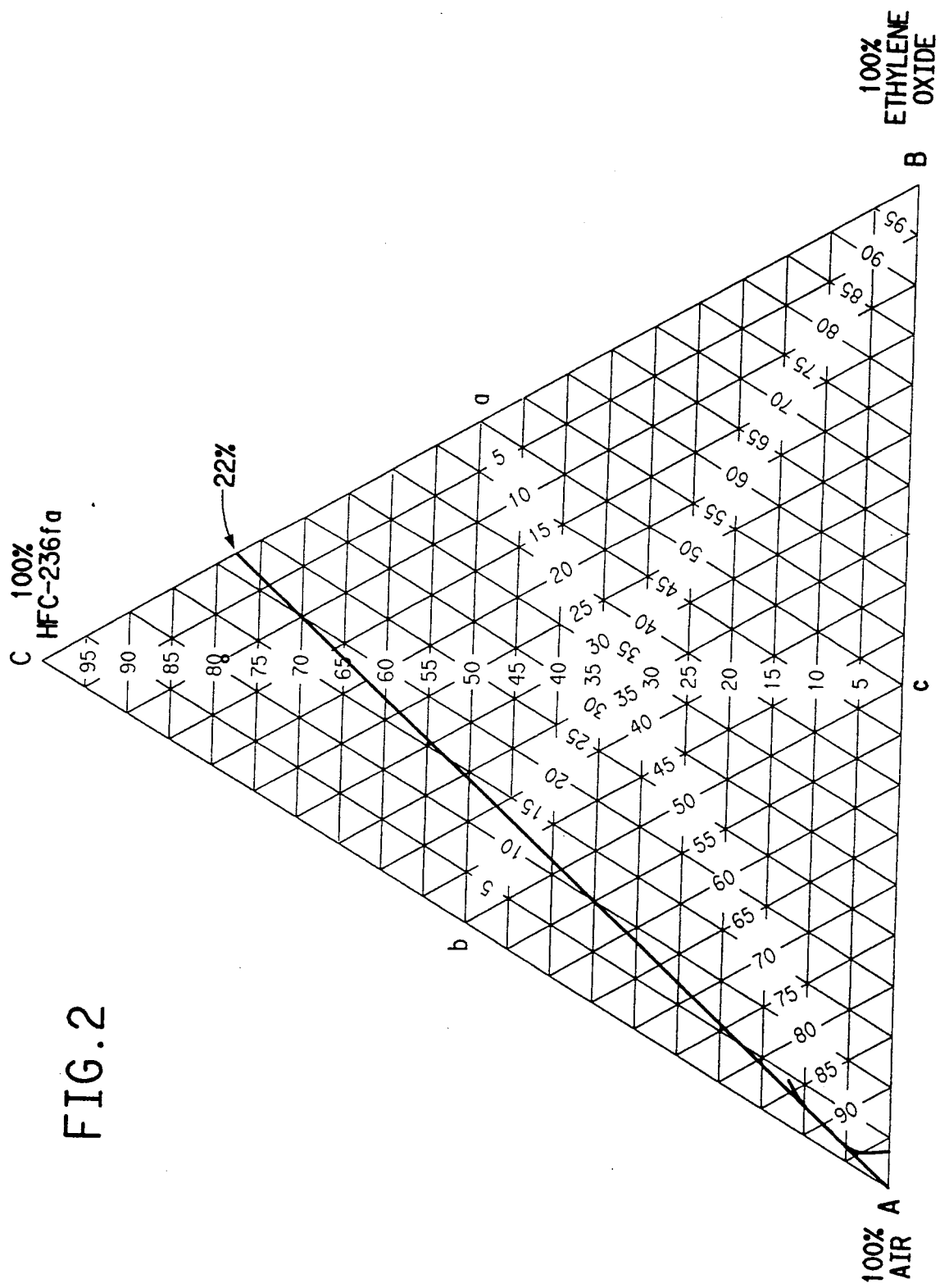
FIG. 2 is a graphical representation of flammability tests for one embodiment of the sterilant mixture of the present invention.

A series of flammability tests were carried out to determine the flammability curve for ethylene oxide intermixed with HFC-236 fa. The procedure was as follows. Ethylene oxide, air and the flame retardant, all at measured concentrations, were mixed in a 5 liter spherical vessel at 98.07 kPa (1 atmosphere) and 25° C. An electrically activated match was placed in the middle of the vessel to provide ignition energy to the mixture. Flammability, i.e. whether or not the mixture ignited, was determined by visual observation of the flame propagation to the vessel wall. The data for various mixtures is shown in FIG. 2 for the HFC-236 fa mixtures. The curve below the tangent line indicates ignition for that particular mixture. The curve shown in FIG. 2 represents the flammability curve for the mixture.

In order for a sterilant mixture to be non-flammable, it must be non-flammable at all concentrations of air, i.e. from 0 to 100 percent air. Thus, a straight line representing 0 to 100 percent air cannot cross below the flammability curve. A straight line from 0 to 100 percent air just tangent to but not crossing below the flammability curve represents the highest ethylene oxide concentration while maintaining the mixture non-flammable. Such straight line is drawn in FIG. 2 and shows that for ethylene oxide HFC-236 fa mixtures, the ethylene oxide concentrations can be up to 22 mole percent and yet the mixture remains non-flammable for all concentrations of air.

EXAMPLE 2

Comparative Example

For comparative purposes, the above-described procedure was repeated except that 1,2,2,2-tetrafluoroethane (HFC-134 a) was used in place of HFC-236 fa.

Figure 3:
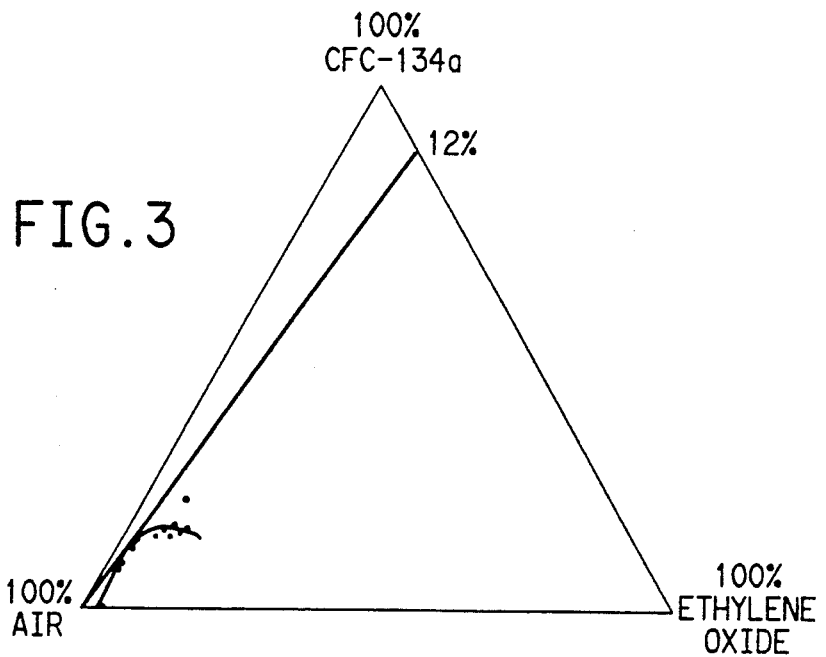
FIG. 3 is a graphical representation of flammability tests for an ethylene oxide mixture formulated with the compound generally accepted as the substitute for CFC-12.

HFC-134a has become generally accepted as the most likely replacement for CFC-12. This data is reported in FIG. 3. As is shown by the data, a mixture of ethylene oxide and HFC-134a is non-flammable only up to a maximum ethylene oxide concentration of 12 percent over the full range of air concentration.

The above Examples 1 and 2 demonstrate that the sterilant gas mixtures of the present invention exhibit a non-flammability nearly double that of the mixture formulated with the widely acknowledged replacement for CFC-12.

EXAMPLE 3

Phase Study

A phase study on the following composition, wherein the composition is varied and the vapor pressure is measured, at a constant temperature of 25° C., shows that the following composition is an azeotrope.

31.6 mole percent ethylene oxide
68.4 mole percent HFC-236 fa
vapor pressure = 44.7 psia (308 kPa)

EXAMPLE 4

Impact of Vapor Leakage on Vapor Pressure at 25° C.

A vessel is charged with an initial composition at 25° C., and the vapor pressure of the composition is measured. The composition is allowed to leak from the vessel, while the temperature is held constant at 25° C., until 50 weight percent of the initial composition has been removed, at which time the vapor pressure of the composition remaining in the vessel is measured. The results are summarized below.

| Ethylene oxide/ HFC-236fa composition (Mole percent) | 0 wt % evaporated psia (kPa) | 50 wt % evaporated psia (kPa) | % change in vapor pressure |
| --- | --- | --- | --- |
| 6.6/93.4 | 42.0 (289) | 40.8 (282) | 2.9 |
| 9.7/90.3 | 42.8 (295) | 41.7 (288) | 2.4 |
| 22.1/77.9 | 44.4 (306) | 44.2 (305) | 0.5 |

-continued

| Ethylene oxide/ HFC-236fa composition (Mole percent) | 0 wt % evaporated psia (kPa) | 50 wt % evaporated psia (kPa) | % change in vapor pressure |
| --- | --- | --- | --- |
| 27.7/72.3 | 44.7 (308) | 44.6 (308) | 0.2 |
| 27.7/72.3 | 44.7 (308) | 44.7 (308) | 0 |
| 37.9/62.1 | 44.6 (308) | 44.5 (307) | 0.2 |
| 46.3/53.7 | 44.2 (305) | 43.6 (301) | 1.4 |
| 53.5/46.5 | 43.7 (301) | 42.3 (292) | 3.2 |
| 59.7/40.3 | 43.1 (297) | 40.5 (280) | 6.0 |
| 65.0/35.0 | 42.3 (292) | 38.2 (263) | 9.7 |

These data show that compositions from 6 to 65 mole percent ethylene oxide and from 35 to 94 mole percent HFC-236 fa are azeotropic or azeotrope-like in that when 50 weight percent of an original composition is removed, the vapor pressure of the composition changes less than about 10 percent.

We claim:

1. A sterilant mixture which comprises from 15 to 30 mole percent ethylene oxide and from 70 to 85 mole percent 1,1,1,3,3,3-hexafluoropropane.

2. A sterilant mixture according to claim 1 wherein the mole percent of ethylene oxide is from 20 to 26 percent.

3. A sterilant mixture according to claim 1 wherein the mole percent of 1,1,1,3,3,3-hexafluoropropane is from 74 to 80 percent.

4. A sterilant mixture according to claim 1 which also comprises chlorodifluoromethane.

5. A sterilant mixture according to claim 1 which also comprises nitrogen.

6. A method for sterilizing an article which comprises contacting the article with a sterilant mixture according to any of claims 1 to 5.

7. A method according to claim 6, wherein the sterilant mixture is in gaseous form when it contacts the article.

8. A composition comprising effective amounts of ethylene oxide and 1,1,1,3,3,3-hexafluoropropane to form an azeotropic or azeotrope-like composition at 25° C. when the pressure is adjusted to substantially atmospheric pressure.

9. The composition of claim 8, comprising 6 to 65 mole percent ethylene oxide and 35 to 94 mole percent 1,1,1,3,3,3-hexafluoropropane.

* * * * *